United States Patent
Wittenstein

(10) Patent No.: US 10,438,695 B1
(45) Date of Patent: Oct. 8, 2019

(54) SEMI-AUTOMATED CLUSTERED CASE RESOLUTION SYSTEM

(71) Applicant: EMC Corporation, Hopkinton, MA (US)

(72) Inventor: Andreas Wittenstein, Granada (ES)

(73) Assignee: EMC IP Holding Company LLC, Hopkinton, MA (US)

( * ) Notice: Subject to any disclaimer, the term of this patent is extended or adjusted under 35 U.S.C. 154(b) by 763 days.

(21) Appl. No.: 14/870,898

(22) Filed: Sep. 30, 2015

(51) Int. Cl.
*G16H 40/20* (2018.01)

(52) U.S. Cl.
CPC .................................. *G16H 40/20* (2018.01)

(58) Field of Classification Search
CPC .......................... G06Q 50/22–24; G06F 19/30
See application file for complete search history.

(56) References Cited

U.S. PATENT DOCUMENTS

| 9,021,583 | B2 | 4/2015 | Wittenstein et al. | |
|---|---|---|---|---|
| 9,690,930 | B1 | 6/2017 | Gulko et al. | |
| 2002/0099571 | A1* | 7/2002 | Waku | G16H 40/20 705/2 |
| 2003/0036684 | A1* | 2/2003 | Hood | A61B 5/7435 600/300 |
| 2005/0149363 | A1* | 7/2005 | Loiterman | G06Q 50/24 705/3 |
| 2008/0201280 | A1* | 8/2008 | Martin | G06Q 50/24 706/12 |
| 2009/0313269 | A1* | 12/2009 | Bachmann | G06F 21/645 |
| 2012/0065987 | A1* | 3/2012 | Farooq | G06F 19/328 705/2 |
| 2013/0297767 | A1* | 11/2013 | Kozine | G06F 11/3447 709/224 |
| 2014/0006292 | A1 | 1/2014 | Kozlovsky et al. | |
| 2014/0122098 | A1* | 5/2014 | Scarasso | G06Q 30/0278 705/2 |
| 2016/0117469 | A1* | 4/2016 | Tesanovic | G16H 50/70 705/3 |
| 2016/0180222 | A1* | 6/2016 | Sierhuis | G06F 7/023 706/47 |

OTHER PUBLICATIONS

Andreas Wittenstein; "Computerized Case Management System With Auto-Generated Memorable Case Identifiers," U.S. Appl. No. 14/868,675, filed Sep. 29, 2015.

* cited by examiner

*Primary Examiner* — Robert A Sorey
(74) *Attorney, Agent, or Firm* — BainwoodHuang

(57) ABSTRACT

A method of efficiently resolving cases within a system includes (a) receiving a set of cases within the system, (b) running an automated clustering agent to automatically create a plurality of clusters of related cases based on similarities between the related cases, each cluster including a plurality of cases, and (c) processing a set of the clusters of cases through a pipelined case cluster resolution system, the pipelined case cluster resolution system including a plurality of computerized agents and at least one human agent operating in a defined order, the pipelined case cluster resolution system resulting in a resolution of each case of a cluster of the plurality of clusters of related cases, each case having a same resolution as each other case in its respective cluster. An apparatus and computer program product for performing a similar method are also provided.

16 Claims, 9 Drawing Sheets

SEMI-AUTOMATED CLUSTERED CASE RESOLUTION SYSTEM

BACKGROUND

Many services, particularly network services such as those provided by websites, regularly deal with huge numbers of cases or incidents, which need to be resolved efficiently, accurately, and quickly. Efficiency is especially important for cases consuming costly resources, such as time spent by scarce expert analysts; and especially during surges in the number of cases. Accuracy is especially important in cases where an inappropriate resolution has fatal or costly consequences; and for decisions having irreversible effects. Quickness is especially important for emergency cases, and for types of cases involving real-time processing or resolution.

Case-management systems have cases pass through several phases of evaluation at different stages in a process leading to resolution. Depending on the case-management system, the current workload, the available personnel, and the individual case, the various phases of the process may be handled by anywhere from a single agent end to end, to a different agent for each phase.

Conventional case-management systems commonly address efficient use of expert time by presenting cases first to agents with low expertise who can process simple and common cases on their own, and can iteratively escalate complicated and rare cases to be reprocessed by agents with ever greater expertise. Efficient use of agents during surges is commonly addressed by adjusting the agent pool according to demand, such as by hiring part-time agents during surges, or by reassigning agents to other tasks during lulls.

Accuracy is commonly addressed by feedback from later stages within and beyond the case workflow; and by having cases cross-checked by peers or spot-checked by experts, especially for more-critical cases.

Quick processing is commonly addressed for urgent cases by early escalation, and for real-time case types by dedicated specialized workflows.

SUMMARY

Unfortunately, despite the use of the above-mentioned and similar conventional techniques to address efficiency, accuracy, and quickness, prior-art case-management systems all leave much room for improvement in each of these three criterial dimensions, mostly due to limitations of their case-by-case approach. Upon completing evaluation of each case, an agent ordinarily moves on to the next case in the priority queue, which may exhibit very different characteristics and behaviors. Although some such variety is important for reducing agent fatigue, each such discontinuity inevitably introduces a delay as the agent reorients to the context of the new case and adapts to its different requirements. Although exposure to different types of cases is important for continuing agent training, frequent unrelatedness of cases successively presented to an agent translates to frequent case-escalation and consequent inefficient reprocessing of cases by higher-level agents. Thus the case-by-case approach hinders both efficient use of agents' time, and quick resolution of individual cases.

In addition, when cross-checking by a peer or spot-checking by a superior reveals an error in an agent's evaluation of a case at any stage, that agent is likely to have made the same error in other cases, as are many other agents who learned from that agent or from whom that agent learned. Depending on the circumstances, some of those errors may still be correctable; in any case, all the errant agents need to be trained to avoid that error thenceforward. Handling cases individually makes it difficult to track down other instances of an error and the agents who produced them. Thus individual-case management hinders accurate case resolution in more than one way.

Upon encountering multiple similar incidents resulting in similar resolutions, an expert may attempt to write a rule to automatically detect such incidents in the future and automatically resolve them. For an administrator to write rules requires a very high level of expertise in the domain as well as in the logic and mathematics of the rules language. In addition, implementing the rules is fraught with potentially catastrophic error by misclassifying too many or even all cases as false-positives or false-negatives, often with irreversible consequences.

Thus, it would be desirable to automatically cluster related cases into clusters that may be resolved all together. This result may be achieved by automatically clustering related cases into clusters according to their expected intermediate and ultimate resolutions and then feeding the clusters into a semi-automated pipelined case cluster resolution system in order to resolve entire clusters of cases at once. Thus, entire groups of cases can be dealt with together rather than individually, and much of the case processing may be done automatically by computer to increase speed and accuracy.

In one embodiment, a method of efficiently resolving cases regarding trouble within a system is performed by a computing device. The method includes (a) receiving a set of cases regarding trouble within the system, (b) running an automated clustering agent to automatically create a plurality of clusters of related cases based on similarities between the related cases, each cluster including a plurality of cases, and (c) processing a set of the clusters of cases through a pipelined case cluster resolution system, the pipelined case cluster resolution system including a plurality of computerized agents and at least one human agent operating in a defined order, the pipelined case cluster resolution system resulting in a resolution of each case of a cluster of the plurality of clusters of related cases, each case having a same resolution as each other case in its respective cluster. An apparatus and computer program product for performing a similar method are also provided.

BRIEF DESCRIPTION OF THE DRAWINGS

The foregoing and other objects, features, and advantages will be apparent from the following description of particular embodiments of the present disclosure, as illustrated in the accompanying drawings in which like reference characters refer to the same parts throughout the different views.

DETAILED DESCRIPTION

Embodiments are directed to techniques to automatically cluster related cases into clusters that may be resolved all together. This result may be achieved by automatically clustering related cases into clusters according to their expected intermediate and ultimate resolutions and then feeding the clusters into a semi-automated pipelined case cluster resolution system in order to resolve entire clusters of cases at once. Thus, entire groups of cases can be dealt with together rather than individually, and much of the case processing may be done automatically by computer to increase speed and accuracy.

Figure 1:
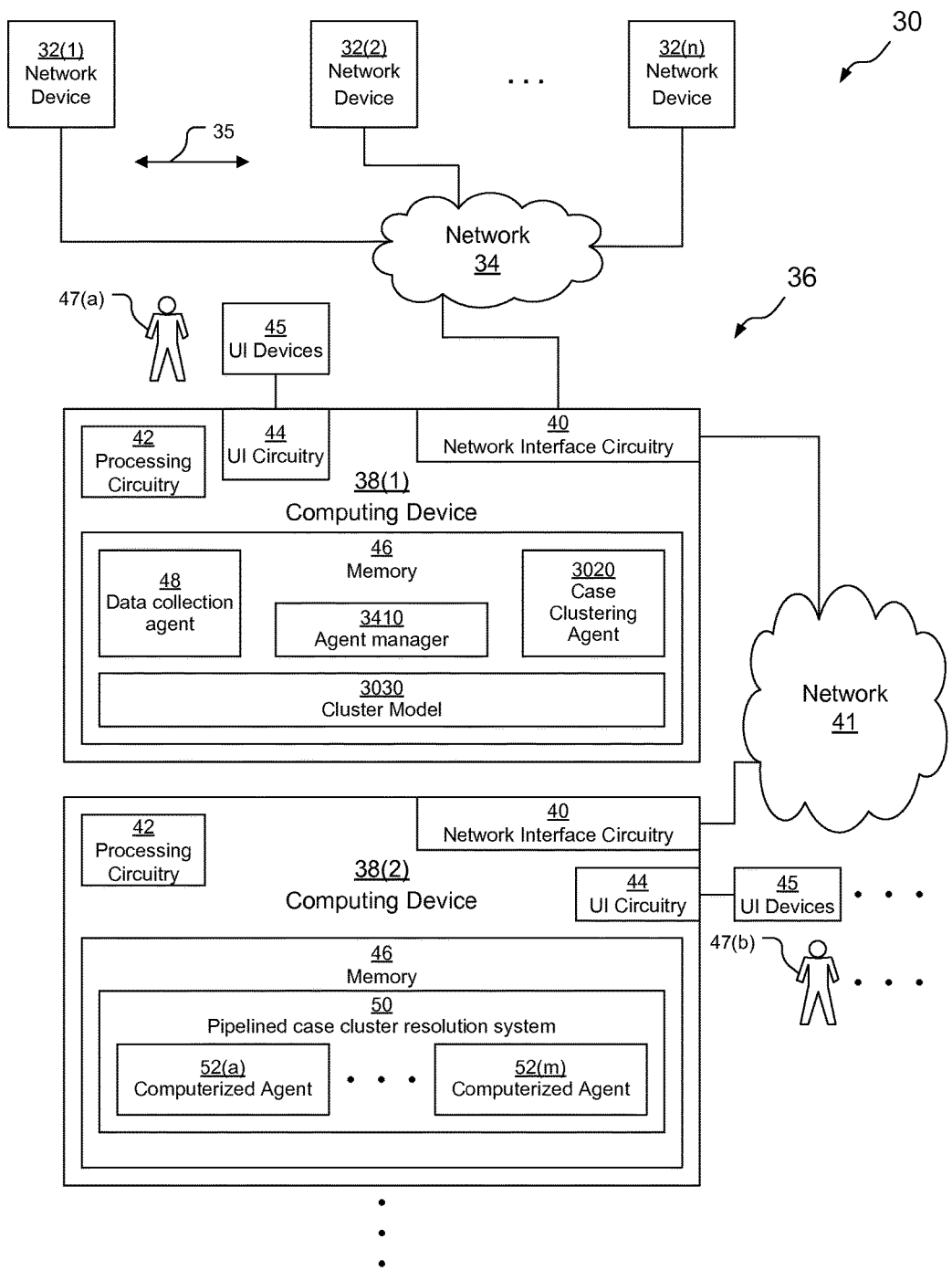
FIG. 1 is a block diagram depicting an example system and apparatus for use in connection with various embodiments.

FIG. 1 depicts a system 30. System 30 may include a set of network devices 32 (depicted as network devices 32(1), 32(2), . . . , 32(n)) connected to a network 34 and an improved case resolution system 36. Network devices 32 may be any kind of computing devices configured to operate on a network, such as, for example, personal computers, workstations, server computers, laptop computers, tablet computers, smart phones, mobile computers, etc. or combinations thereof. Network 34 may be any kind of computer network including, for example, a local area network, a wide area network, a storage area network, a virtual private network, a cellular data network, a set of point-to-point connections, a fabric of interconnected connections and switches, etc. or combinations thereof. Network traffic 35 may flow across network 34.

Case resolution system 36 includes a set of one or more computing devices 38 (depicted as computing devices 38(1), 38(2), . . . ) interconnected by a network 41. Network 41 may be similar to network 34. In some embodiments, network 41 may be replaced by network 34. In some embodiments, network 41 may be omitted altogether (e.g., if case resolution system 36 includes only a single computing device 38).

Each computing device 38 includes network interface circuitry 40, processing circuitry 42, memory 46, and, optionally, user interface (UI) circuitry 44. At least one of the computing devices 38 of the case resolution system 36 includes UI circuitry 44. Network interface circuitry 40 may include one or more Ethernet cards, cellular modems, Fibre Channel (FC) adapters, Wireless Fidelity (Wi-Fi) wireless networking adapters, and other devices for connecting to a network 34, 41, etc.

Processing circuitry 42 may be any kind of processor or set of processors configured to perform operations, such as, for example, a microprocessor, a multi-core microprocessor, a digital signal processor, a system on a chip, a collection of electronic circuits, a similar kind of controller, or any combination of the above.

UI circuitry 44 contains circuitry for interfacing with one or more UI devices 45 that allow one or more human agents 47 (depicted as human agents 47(a), 47(b), . . . ) to input and receive data to and from the computing devices 38. For example, UI circuitry 44 may include a serial bus adapter, a graphics adapter, etc., while UI devices 77 may include one or more of a display device (e.g., a CRT, LCD, plasma, or LED monitor) and an input device (e.g., a mouse, trackpad, tracking stick, keyboard, keypad, microphone, biometric sensor, etc.).

Memory 46 may be any kind of digital system memory, such as, for example, random access memory (RAM). Memory 46 stores one or more operating systems in operation (not depicted, e.g., Linux, UNIX, Windows, or a similar operating system), various storage system management programs in operation (not depicted), and one or more applications executing on processing circuitry 42 as well as data used by those applications.

As depicted, memory 46 of computing device 38(1) includes data collection agent 48, agent manager 3410, case clustering agent 3020, and cluster model 3030, while memory 46 of computing device 38(2) includes pipelined case cluster resolution system 50, which includes a set of computerized agents 52 (depicted as computerized agents 52(a), . . . , 52(m)). However, these software and data components 48, 3410, 3020, 3030, 50, 52 may be distributed among the one or more computing devices 38 in other configurations. Typically, data collection agent 48 runs on a computing device 38(1) that connects to network 34, while the remaining elements 3410, 3020, 3030, 50, 52 may run or be stored all on the same computing device 38(1), all on other computing devices 38, or on a combination thereof.

In some embodiments, memory 46 may also include a persistent storage portion (not depicted). Persistent storage may be made up of one or more persistent storage devices, such as, for example, hard disk drives, solid-state storage devices, flash drives, etc. Persistent storage is configured to store programs and data even while the computing device 38 is powered off. The OS (e.g., Linux, UNIX, Windows, or a similar operating system) and the applications (e.g., agents 48, 3410, 3020, 52) are typically stored in persistent storage so that they may be loaded into memory 46 from persistent storage upon a system restart. These applications, when stored in non-transient form either in the volatile portion of memory 46 or in persistent storage, form a computer program product. The processing circuitry 42 running one or more of these applications thus forms a specialized circuit constructed and arranged to carry out the various processes described herein.

It should be understood that, in some embodiments, case resolution system 36 may operate in the context of a system 30 that does not involve network 34 in an integral sense. For example, system 30 may include a hospital triage system or a hospital treatment system. Although a hospital may operate a network, case resolution system 36 may, instead of interfacing with a network 34, interface with a user terminal into which a nurse or doctor enters medical case information, thereby generating a set of cases to be resolved by diagnosis and treatment plans.

Figure 2A:
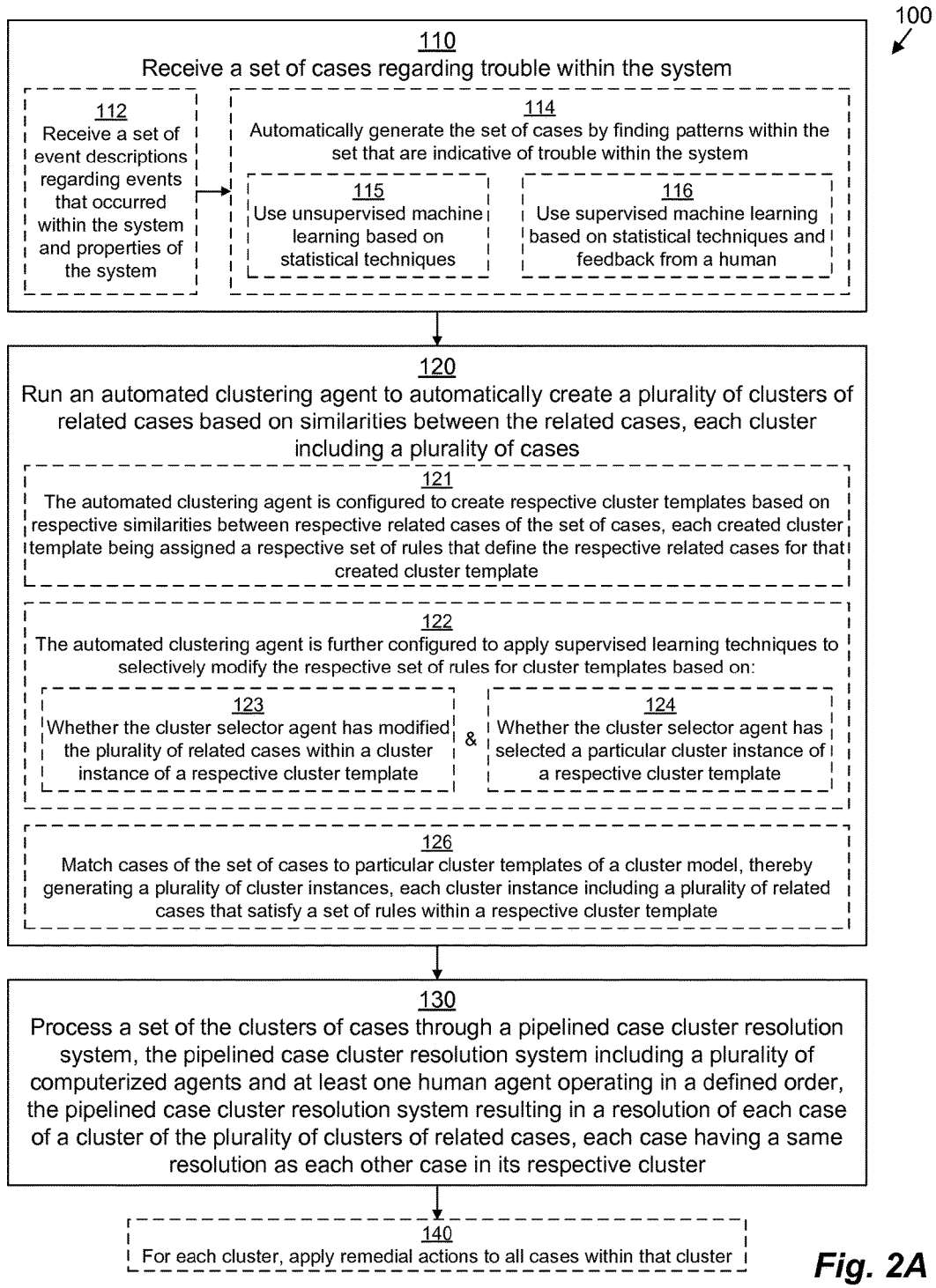
FIGS. 2A-2B are flowcharts depicting an example method according to various embodiments.
Figure 2B:
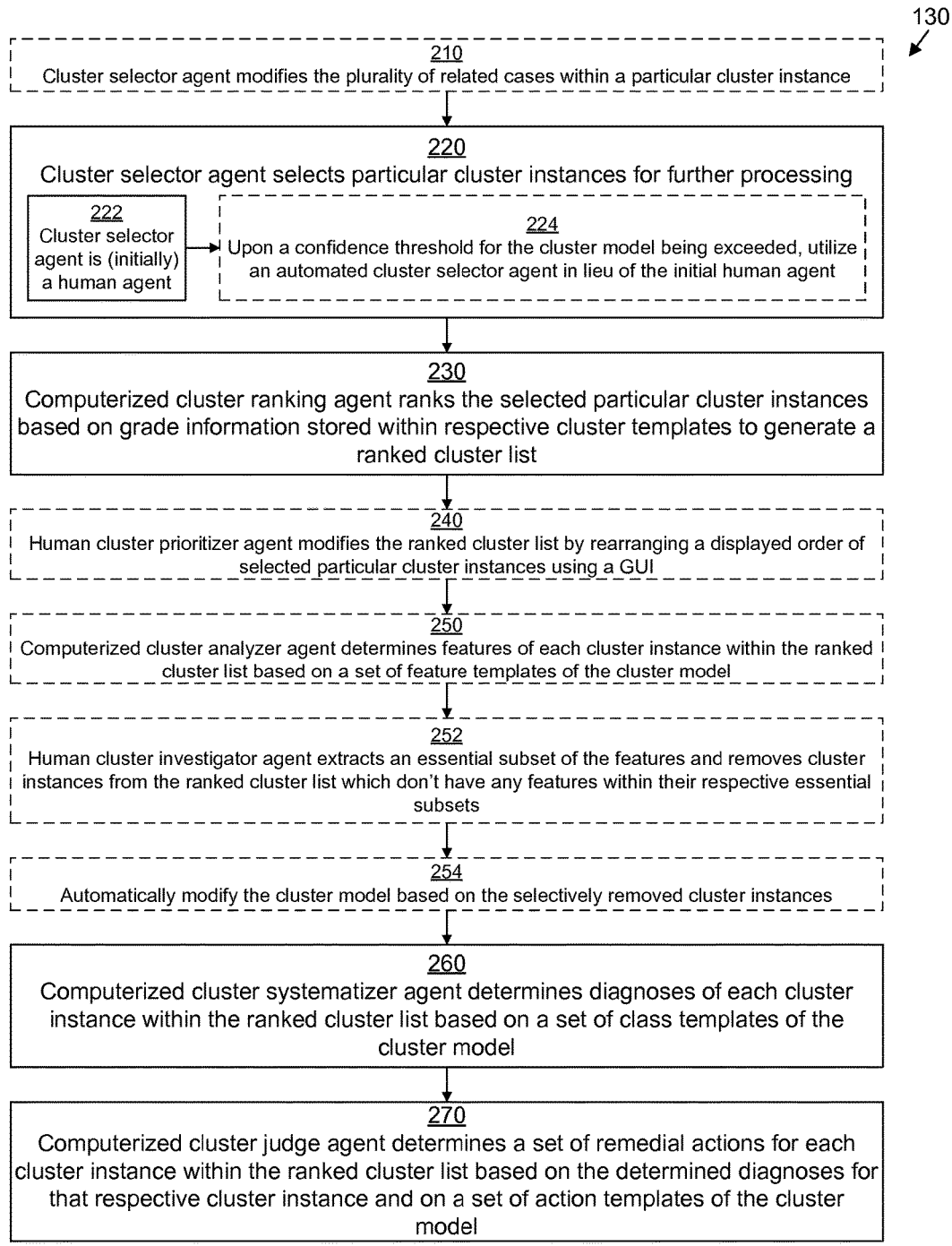

FIGS. 2A and 2B illustrates an example method 100 performed by case resolution system 36 to automatically cluster related cases into clusters that may be resolved all together. It should be understood that any time a piece of software (e.g., agent 48, 3410, 3020, 52, etc.) is described as performing a method, process, step, or function, in actuality what is meant is that a computing device 38 or distributed computing system (e.g., case resolution system 36) on which that piece of software is running performs the method, process, step, or function when executing that piece of software on its processing circuitry 42. It should be understood that although depicted in one order, one or more steps or sub-steps may be combined together or performed in a different order. It should be understood that, within FIG. 2, various sub-steps are dashed because they may be optional and not fundamental to method 100. However, it should be understood that, in some embodiments, one or more of the other steps may also be omitted. Similarly, in some embodiments, one or more steps may be combined together or performed in a different order.

In step 110, case resolution system 36 receives a set of cases 2040 (see FIG. 3, below) within system 30. In some embodiments, these cases may be network irregularities, while in other embodiments, these may be reports of symptoms by patients in a hospital, for example.

In some embodiments, the set of cases 2040 may be generated by performance of sub-steps 112 and 114. In sub-step 112, data collector agent 48, executing on computing device 38(1) receives a set of event descriptions regarding events that occurred within the system 30 as well as properties of the system 30. In some embodiments, data collector agent 48 may function as a full IP capture packet sniffer, capturing all network traffic 35, while in other embodiments, data collector agent 48 may record metadata regarding all packets that are transmitted over network 34 (e.g., packet source and target addresses as well as certain other information about the contents of at least some of the packets).

In sub-step 114, data collector agent 48 or another software component may automatically generate the set of cases 2040 by finding patterns within the set of event descriptions and properties with the system 30. In some embodiments (sub-sub-step 115), sub-step 114 is performed by employing unsupervised machine learning based on statistical techniques. In other embodiments (sub-sub-step 116), sub-step 114 is performed by employing supervised machine learning based on statistical techniques as well as feedback from a human agent, such as human agent 47(a).

In step 120, case resolution system 36 (e.g., computing device 38(1)) runs an automated case clustering agent 3020 to automatically create a plurality of cluster instances 3050 (see FIG. 3, below) of related cases 2040 based on similarities between the related cases, each cluster 3050 including a plurality of cases 2040 (see cluster paradigm 4080 within cluster template 4050 that stores a set of cases 4090 in FIG. 4, below).

In some embodiments, the automated case clustering agent 3020 is configured (sub-step 121) to create respective cluster templates 4050 within cluster model 3030 based on respective similarities between respective related cases 2040 of the set of cases 2040, each created cluster template 4050 being assigned a respective set of rules that define the respective related cases 4090 for that created cluster template 4050. This set of rules may be, for example, the cluster definition 4100 of the cluster template 4050.

In some embodiments, the automated clustering agent 3020 is further configured (sub-step 122) to apply supervised learning techniques to selectively modify the respective set of rules for cluster templates 4050 based on various factors. In one embodiment, both conditions 123 and 124 are considered. Condition 123 determines whether a cluster selector agent 3060 (see FIG. 4) has modified the plurality of related cases 2040 (e.g., within cluster sample 4200, see FIG. 4) within a cluster instance 3050 of a respective cluster template 4050. Condition 124 determines whether the cluster selector agent 3060 has selected a particular cluster instance 3050 of a respective cluster template 4050 for inclusion within a selected cluster pool 3070 as a selected cluster instance 3080 (see FIG. 4).

In some embodiments, in sub-step 126, the automated clustering agent 3020 matches cases 2040 of the set of cases (e.g., case stream 2030, see FIG. 3) to particular cluster templates 4050 of the cluster model 3030, thereby generating the plurality of cluster instances 3050, each cluster instance 3050 including a plurality of related cases 2040 within cluster sample 4200 that satisfy a set of rules (e.g., cluster definition 4100) within a respective cluster template 4050.

After step 120, in step 130, case resolution system 36 processes a set (e.g., cluster pool 3040, see FIG. 4) of the clusters 3050 of cases through a pipelined case cluster resolution system 50, the pipelined case cluster resolution system 50 including a plurality of computerized agents 52 and at least one human agent 47 operating in a defined order, the pipelined case cluster resolution system 50 resulting in a resolution of each case 2040 of a cluster 3050 of the plurality of clusters of related cases, each case 2040 having a same resolution as each other case 2040 in its respective cluster 3050. Step 130 is depicted in further detail below in connection with FIG. 2B.

Finally, in step 140, case resolution system 36 applies remedial actions to all cases 2040 within each processed cluster 3050 as determined by the output of the pipelined case cluster resolution system 50.

FIG. 2B depicts various sub-steps within step 130 according to various embodiments. Sub-steps 210, 240, 250, 252, and 254 as well as sub-sub-step 222 are depicted as optional, although, in some embodiments, other sub-steps and sub-sub-steps may be omitted or added as well.

In sub-step 210, cluster selector agent 3060 modifies the plurality of related cases within a particular cluster instance 3050. Thus, cluster selector agent 3060 may modify the selection of cases 2040 within the cluster sample 4200 of a cluster instance 3050. This action may affect the cluster paradigm 4080 (see FIG. 4) and related cluster definition 4100 of the cluster template 4050 that initially defined the cluster instance 3050 (see sub-step 122 and condition 123).

In sub-step 220, cluster selector agent 3060 selects particular cluster instances 3050 as selected cluster instances 3080 for further processing and inclusion within selected cluster pool 3070. This action may affect the cluster definition 4100 of the cluster template 4050 that initially defined the cluster instance 3050 (see sub-step 122 and condition 124) as well as various other features of that cluster template 4050.

It should be understood, as indicated in sub-sub-step 222, that cluster selector agent 3060 is, at least initially, a human agent 47. However, as time progresses, and the certainty of the cluster definition 4100 increases as the model 303 becomes more accurate, in some embodiments, sub-sub-step 224 may be performed, in which the cluster selector agent 3060 transitions to become an automated agent 52 once a confidence threshold for the cluster model 3030 becomes exceeded.

Figure 3:
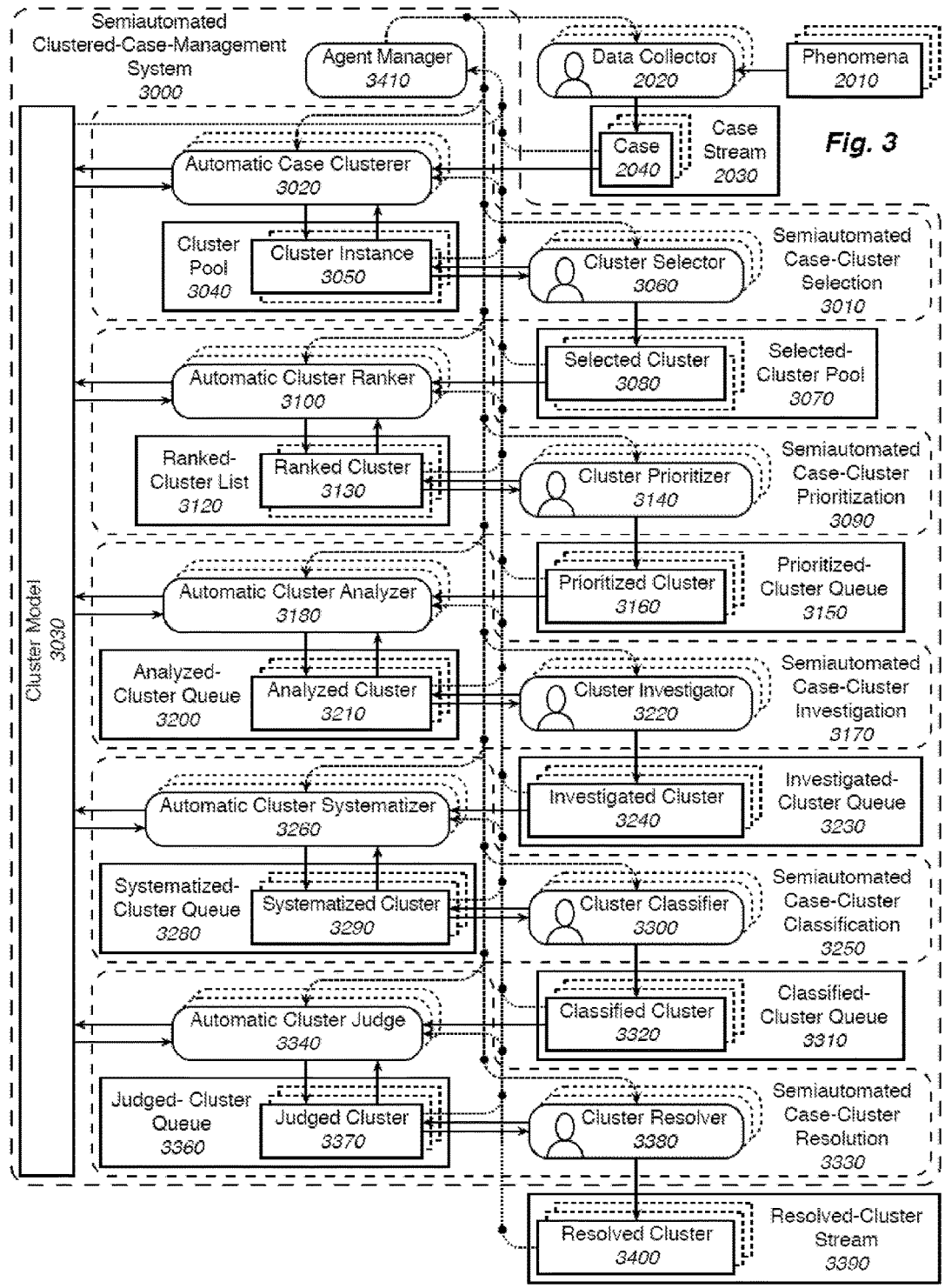
FIG. 3 is a block diagram depicting an example pipelined case cluster resolution system for use in connection with various embodiments.
Figure 5:
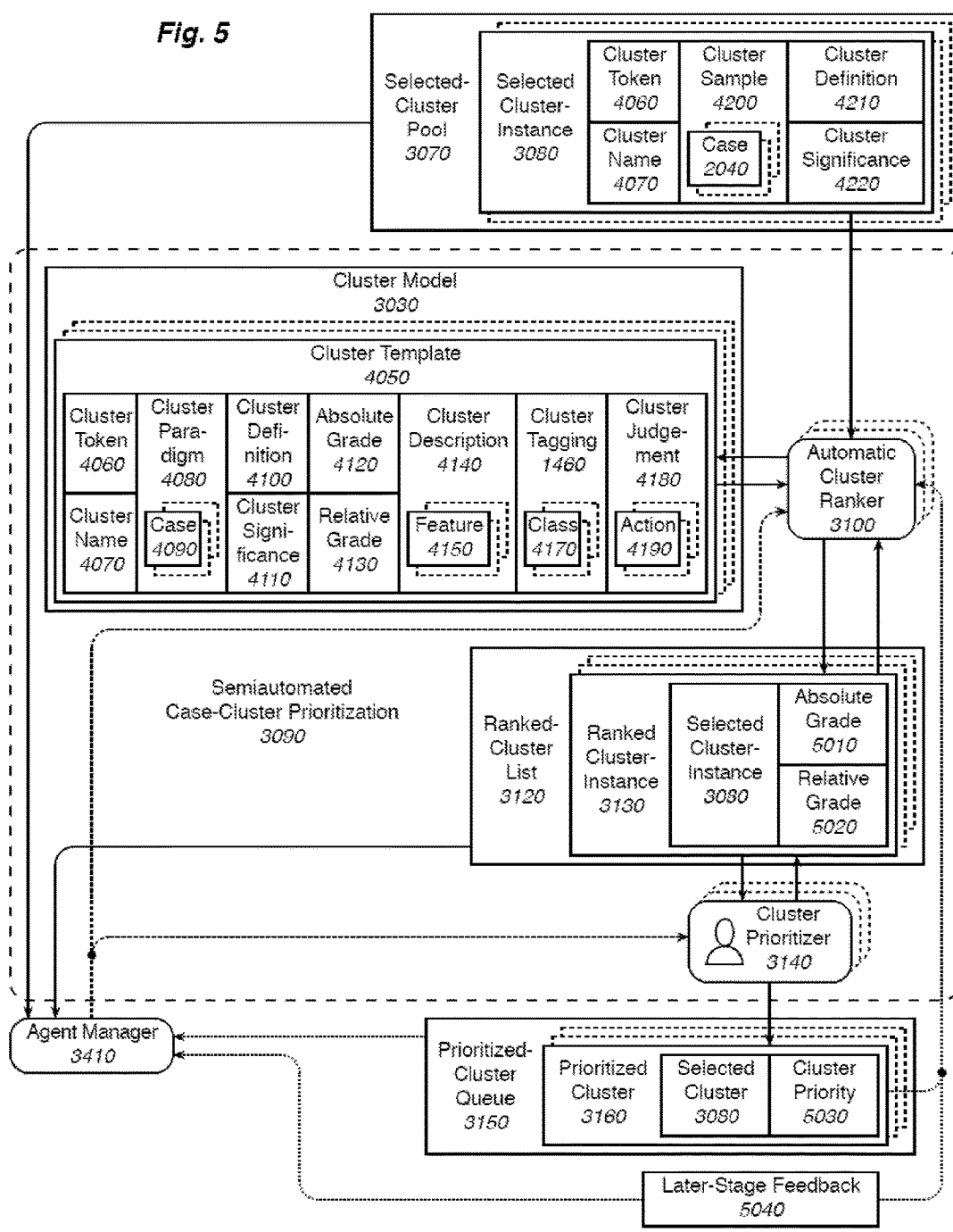
FIG. 5 is a block diagram depicting a detailed view of an example portion of a pipelined case cluster resolution system for use in connection with various embodiments.

In sub-step 230, a computerized cluster ranking agent 52 (e.g., automatic cluster ranker 3100, see FIGS. 3 and 5) ranks the selected cluster instances 3080 of the selected cluster pool 3070 based on grade information (e.g., absolute grade 4120 and relative grade 4130, see FIG. 5) stored within their respective cluster templates 4050 to generate a ranked cluster list 3120, made up of a set of ranked cluster instances 3130 in an order (see FIGS. 3 and 5).

In some embodiments, a human agent 47 operating as a cluster prioritizer agent 3140 (see FIGS. 3 and 5) modifies (sub-step 240) the ranked cluster list 3120 by rearranging a displayed order of the ranked cluster instances 3130 using a graphical user interface (GUI) displayed on a UI device 45. Thus, automatic cluster ranker 3100 or some other element of the pipelined case cluster resolution system 50 displays an ordered list of the ranked cluster instances 3130 as ordered within the ranked cluster list 3120, and the human cluster prioritizer agent 3140 can drag and drop the ranked cluster instances 3130 within that list, thereby generating a prioritized cluster queue 3150. In some embodiments (not depicted), the actions of the human cluster prioritizer agent 3140 can feed back to affect the absolute grade 4120 and relative grade 4130 of the respective cluster templates 4050 in a supervised learning manner.

Figure 6:
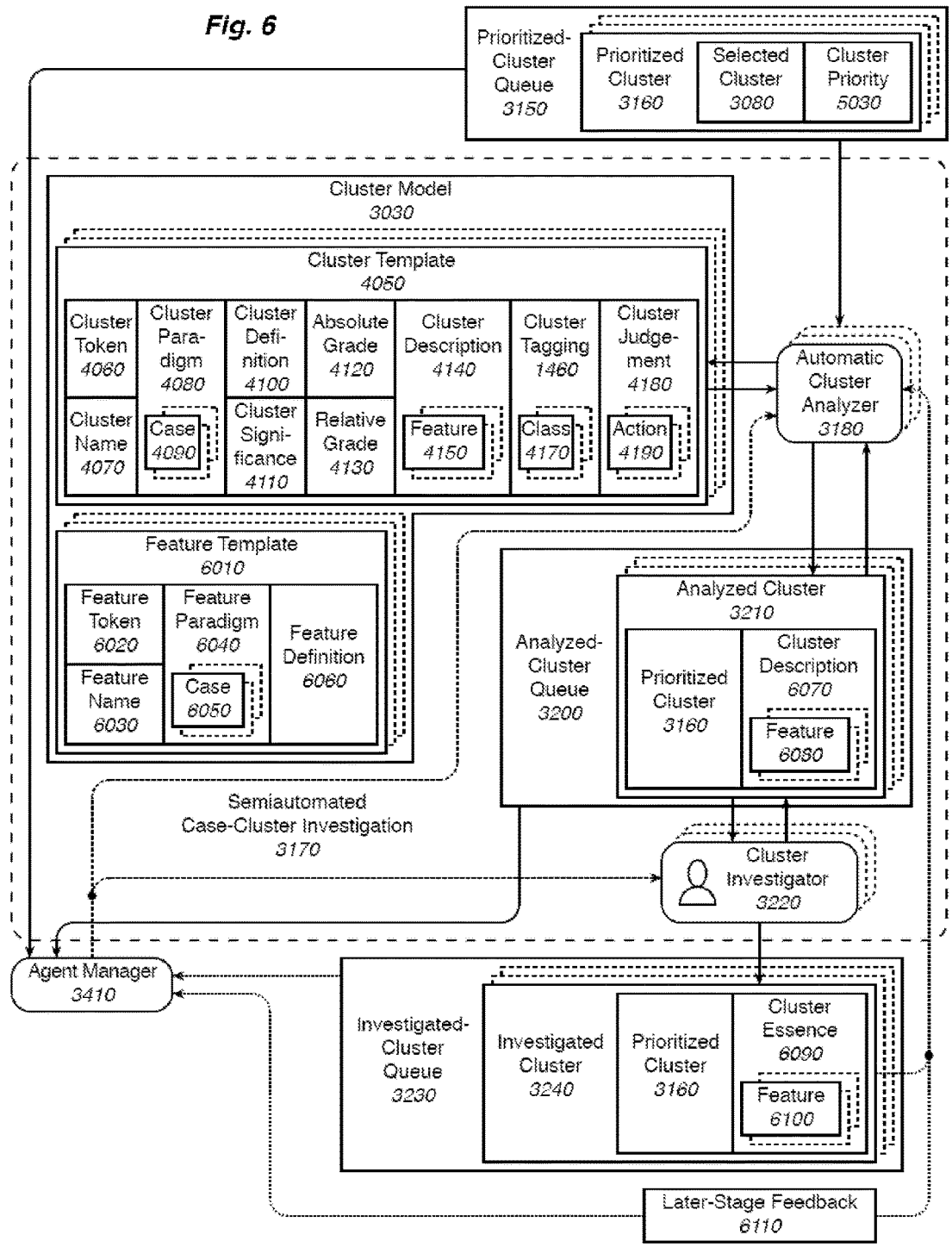
FIG. 6 is a block diagram depicting a detailed view of an example portion of a pipelined case cluster resolution system for use in connection with various embodiments.

In some embodiments, in sub-step 250, a computerized cluster analyzer agent 52 (e.g., automatic cluster analyzer 3180, see FIGS. 3 and 6) determines features 6080 of each cluster instance within the ranked cluster list 3120 (or prioritized cluster queue 3150 if sub-step 240 has been performed) based on a set of feature templates 6010 of the cluster model 3030 (see FIG. 6). Thus, each cluster template 4050 may include a set of features 4150 within a cluster description 4140, each feature 4150 defined by a feature template 6010 of the cluster model 3030. The automatic cluster analyzer 3180 may then apply the features 4150 within the cluster description 4140 of the respective cluster template 4050 to each prioritized cluster 3160 within the prioritized cluster queue 3150 to generate a cluster description 6070 for that prioritized cluster 3160, each cluster description 6070 including a set of features 6080. Feature templates 6010 define features 4150, 6080, which are behaviors of particular cases 2040 that tend to be common. An example feature 4150, 6080 may be "beaconing," whereby a malicious piece of software sends a periodic (or non-periodic) signal to a command and control center, allowing the command and control center to break through a firewall. In the context of a hospital diagnosis system, an example feature 4150, 6080 may be a symptom associated with a disease. Thus, features associated with a heart attack may include chest pain, arm pain, shortness of breath, etc.

In some embodiments, a human agent 47 operating as a cluster investigator agent 3220 (see FIGS. 3 and 6) extracts (sub-step 252) an essential subset of the features 6080 associated with each prioritized cluster 3160 and removes prioritized cluster instances 3160 from an analyzed cluster queue 3200 which don't have any essential features 6100, thereby generating an investigated cluster queue 3230, made up of investigated clusters 3240. Thus, the cluster investigator agent 3220 may note various features 6080 including symptoms of chest pain, arm pain, shortness of breath, hunger, and acne, but recognize that the hunger and acne are not essential features 6100. This step may involve human judgement. In some embodiments (sub-step 254), the actions of the human cluster investigator agent 3220 can feed back to affect the cluster description 4140 of the respective cluster templates 4050 and the feature definitions 6060 of feature templates 6010 in a supervised learning manner.

Figure 7:
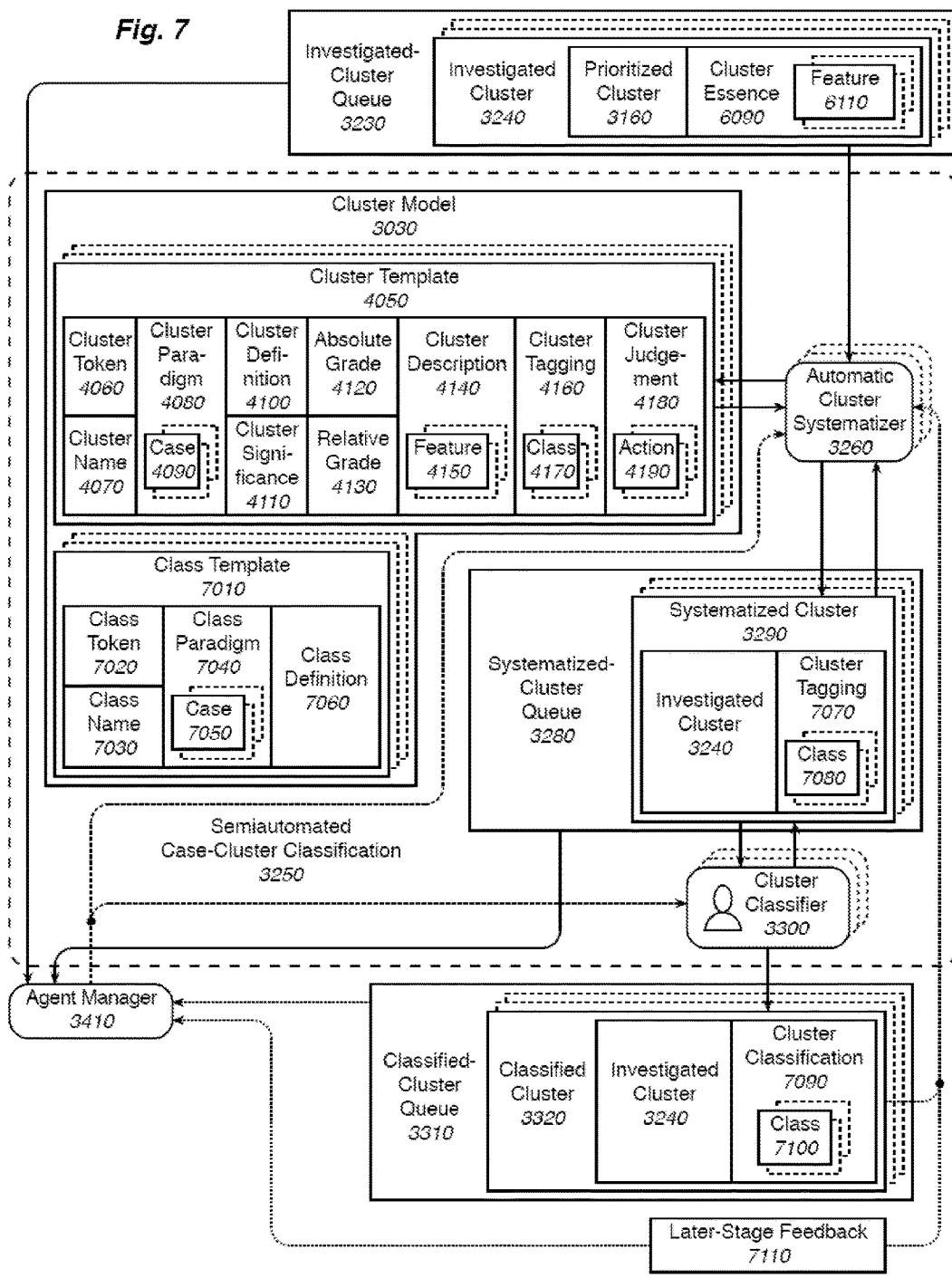
FIG. 7 is a block diagram depicting a detailed view of an example portion of a pipelined case cluster resolution system for use in connection with various embodiments.

In sub-step 260, a computerized cluster systematizer agent 52 (e.g., automatic cluster systematizer agent 3260, see FIGS. 3 and 7) determines classes 7080 of each cluster instance within the ranked cluster list 3120 (or investigated cluster queue 3230 if sub-step 252 has been performed) based on a set of class templates 7010 of the cluster model 3030 (see FIG. 7). Thus, each cluster template 4050 may include a set of classes 4170 within a cluster tagging 4160, each class 4170 defined by a class template 7010 of the cluster model 3030. The automatic cluster systematizer 3260 may then apply the classes 4170 within the cluster tagging 4160 of the respective cluster template 4050 to each investigated cluster 3240 within the investigated cluster queue 3230 to generate a cluster tagging 7070 for that investigated cluster 3240, each cluster tagging 7070 including a set of classes 7080. Class templates 7010 define classes 4170, 7080, which are diagnoses of particular problems associated with particular sets of feature templates 6010. An example class 4170, 7080 may be a Trojan Horse software infection. In the context of a hospital diagnosis system, an example class 4170, 7080 may be a particular disease, such as a heart attack.

In some embodiments (not depicted in FIG. 2B), a human agent 47 operating as a cluster classifier agent 3300 (see FIGS. 3 and 7) extracts some of the classes 7080 associated with each investigated cluster 3240 in order to obtain a primary class 7100 (or several primary classes 7100) for each investigated cluster 3240. Thus, if an investigated cluster 3240 has classes 7080 for heart attack, cancer, acne, and a small scrape, cluster classifier agent 3300 may identify only the heart attack and cancer as primary classes 7100. In some embodiments, the actions of the human cluster classifier agent 3300 can feed back to affect the cluster tagging 4170 of the respective cluster templates 4050 and the class definitions 7060 of class templates 7010 in a supervised learning manner.

Figure 8:
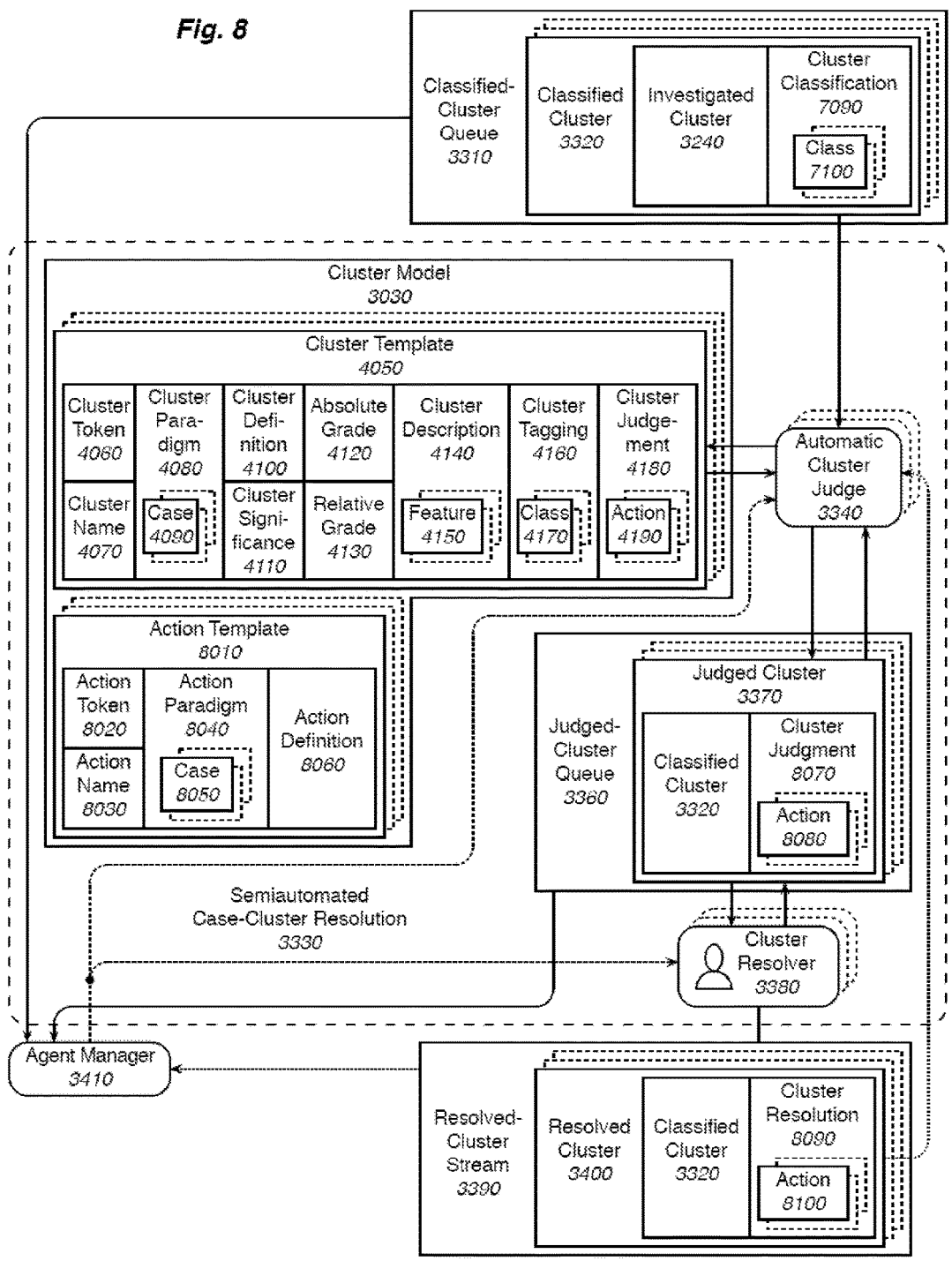
FIG. 8 is a block diagram depicting a detailed view of an example portion of a pipelined case cluster resolution system for use in connection with various embodiments.

Finally, in sub-step 270, a computerized cluster judge agent 52 (e.g., automatic cluster judge agent 3340, see FIGS. 3 and 8) determines a set of remedial actions 8080 for each cluster instance within the classified cluster queue 3310 or systematized cluster queue 3280 based on the determined diagnoses (classes 7080) for that respective cluster instance and on a set of action templates 8010 of the cluster model 3030 (see FIG. 8). Thus, each cluster template 4050 may include a set of remedial actions 4190 within a cluster judgment 4180, each remedial action 4190 defined by an action template 8010 of the cluster model 3030. The automatic cluster judge 3340 may then assign the remedial actions 4190 within the cluster judgment 4180 of the respective cluster template 4050 to each classified cluster 3320 within the classified cluster queue 3310 to generate a cluster judgment 8070 for that classified cluster 3320, each cluster judgment 8070 including a set of remedial actions 8080. Action templates 8010 define remedial actions 4190, 8080, which are treatments of particular diagnoses associated with particular sets of class templates 7010. An example remedial action 4190, 8080 may be quarantining an identified Trojan Horse infected file. In the context of a hospital diagnosis system, an example remedial action 4190, 8080 may be a particular treatment, such as administration of a drug.

In some embodiments (not depicted in FIG. 2B), a human agent 47 operating as a cluster resolver agent 3380 (see FIGS. 3 and 8) extracts some of the remedial actions 8080 associated with each classified cluster 3320 in order to obtain a primary remedial action 8100 (or several primary remedial actions 8100) for each classified cluster 3320. Thus, if a classified cluster 3320 has remedial actions 8080 for administration of nitroglycerine and applying defibrillation, the human cluster resolver agent 3380 may select between those options as appropriate to determine the primary remedial action 8100. In some embodiments, the actions of the human cluster resolver agent 3380 can feed back to affect the cluster judgment 4180 of the respective cluster templates 4050 and the action definitions 8060 of action templates 8010 in a supervised learning manner.

FIGS. 3-8 illustrate details of an example pipelined case cluster resolution system 50 in more detail.

Information-flow diagram FIG. 3 depicts a semi-automated cluster-management system 3000, divided into various stages—selection 3010, prioritization 3090, investigation 3170, classification 3250, resolution 3330—operating on entire clusters of similar cases at a time, with initial evaluation at each stage (illustrated on the left side of the diagram) invariably performed by automated agents 52 (e.g., 3020, 3100, 3180, 3260, 3340), and final evaluation at each stage (illustrated on the right side of the diagram) performed either by automated agents 52, or, when necessary, by human agents 47. Thus, agents 3060, 3140, 3220, 3300, and 3380 may be human. Generally, at least one of these agents is human. In some embodiments, one or more of the stages 3090, 3170, 3250, 3330 or their respective constituent agents 47, 52 may be omitted from semi-automated pipelined case cluster resolution system 50 or the order may be modified.

Thus, in semi-automated clustered-case-management system 3000 phenomena 2010 are measured and recorded by one or more data collectors 2020 collecting information into a stream 2030 of cases 2040 such as web sessions. Instead of manually selecting individual cases 2040, automatic case clusterers 3020 use cluster model 3030 to assign individual incoming cases 2040 to case-cluster instances 3050 in case-cluster pool 3040. Cluster selectors 3060, either human or automatic, consider entire cluster instances at a time, optionally edit them, and transfer the resulting clusters to selected-cluster pool 3070 as selected case-clusters 3080. Any edits by a cluster selector to a cluster instance cause the case-clusterer to adjust the cluster model accordingly.

Similarly, in semi-automated cluster-prioritization phase 3090, instead of manually prioritizing one selected case at a time, automatic cluster-rankers 3100, in accordance with cluster-grade model 3110, automatically rank entire selected clusters 3080 of cases at a time as ranked case-clusters 3130 in ranked-cluster list 3120. Correspondingly, a cluster prioritizer 3140 considers an entire ranked cluster of cases at a time, optionally edits it (thus causing the cluster ranker to adapt the cluster-grade model), and inserts the resulting cluster according to its priority into prioritized-cluster queue 3150 as prioritized case-cluster 3160.

Likewise, in semi-automated cluster-investigation stage 3170, rather than personally investigating just the single highest-priority case at a time, the entire top-priority cluster 3160 of cases is automatically analyzed at once by an automatic cluster analyzer 3180 using cluster-analysis model 3190, adding the corresponding analyzed case-cluster 3210 to analyzed-cluster queue 3200. Cluster investigators 3220 investigate entire analyzed clusters of cases at a time, optionally edit them (consequently causing the cluster analyzer to modify the cluster-analysis model in accordance), and add the resulting clusters to investigated-cluster queue 3230 as investigated case-clusters 3240.

In similar fashion, in semi-automated cluster-classification stage 3250, instead of manually classifying each individual investigated case, automatic cluster systematizers 3260 use cluster-system model 3270 to systematize entire investigated clusters 3240 of cases at once as systematized clusters 3290 in systematized-cluster queue 3280. These systematized clusters of cases are classified in their entirety by cluster classifiers 3300, optionally edited by them (with resultant adjustment of the cluster-system model by the cluster systematizer) and added by them as classified case-clusters 3320 to classified-cluster queue 3310.

Finally, in semi-automated cluster-resolution stage 3330, rather than resolving one classified case at a time by hand, automatic cluster-judges 3340, based on cluster-judgment model 3350, judge entire classified clusters 3320 of cases at once, optionally editing them, and add them as judged case-clusters 3370 in judged-cluster queue 3360. These judged clusters of cases are then resolved in their entirety by cluster resolvers 3380, yielding resolved-cluster stream 3390 of resolved case-clusters 3400. As in the other stages, any edits result in adaptation of the cluster judgment model by the cluster judges.

The processing stages are pipelined in assembly-line fashion, so that as each case-cluster is handed off to be processed in the next stage, the agent handing it off can already begin on the next cluster of cases, with agents at the various stages working in turn on the same cluster as it advances through the pipeline, and working concurrently on different clusters.

The agents 52 operating at the various stages illustrated are not necessarily distinct: An individual agent 52 may, under the control of agent manager 3410, operate at more than one processing stage or even all processing stages for a given cluster, type of cluster, or in general—for example for efficient utilization of an agent 52 competent in plural successive phases, for training an agent 52 in adjacent phases, or when insufficient agents 52 specialized for a phase are available. Equivalently, successive processing stages may be merged for some or all clusters or cluster types for some or all agents.

In each processing phase, plural agents may operate concurrently on different case-clusters, using standard techniques to prevent cluster collisions and resource contention.

In each processing phase, more than one agent may collaborate on a cluster, for example for new or complex types of case-clusters, or for training purposes. Conversely, although a human agent 47 editing a cluster may remove or reassign individual cases from the cluster, a human agent ordinarily acts on each cluster in its entirety.

Moreover, in an application such as an incident-management system, in which only qualifying cases need to be thoroughly processed, an agent 47, 52 at any stage may eject a cluster from the pipeline as not meriting further processing, or, equivalently, may assign it to a null-resolution cluster.

Agent manager 3410 monitors the progress, accuracy, and capabilities of each agent 47, 52 in the clustered-case-management system by tracking the input and output case-clusters in each processing phase (dotted arcs), and presents clusters to appropriate agents 47, 52 accordingly (dashed arcs). For example, if an agent 47, 52 is taking longer than expected to deal with a cluster, explicitly asks for assistance, or is being trained on an unfamiliar type of cluster, the agent manager 3410 may assign additional agents to collaborate on the cluster. If an agent's work on a cluster is interrupted by a more-urgent cluster, a respite, or any other reason, the agent manager 3410 may hold it for later completion by the same agent 47, 52, or assign the cluster to a different agent 47, 52. If an agent 47, 52 has finished dealing with a cluster, and that cluster type is unfamiliar to the agent 47, 52 or the agent 47, 52 explicitly requests confirmation, the agent manager 3410 may feed it back for corroboration by a peer, or for escalation to a more-expert agent 47, 52. If an agent 47, 52 at a later stage revises a decision made at an earlier stage, the agent manager 3410 may return the cluster to the earlier stage for training purposes.

In each processing phase, the invariably automatic pre-processing agents 52 (e.g., automatic case clusterers 3020, automatic cluster rankers 3100, automatic cluster analyzers 3180, automatic cluster systematizers 3260, and automatic cluster judges 3340) predict the decisions made by the optionally human decision agents 47 (e.g. human cluster selectors 3060, human cluster prioritizers 3140, human cluster investigators 3220, human cluster classifiers 3300, and human cluster resolvers 3380). These predictions are refined by supervised learning from the actual human decisions on prior instances of the same and similar clusters. When the accuracy of the prediction for a cluster in a processing phase reaches a configurable threshold of certainty, the agent manager 3410 substitutes automatic decision agents 52 for human agents 47, to increase cluster-processing speed and conserve human-agent processing time.

Although accuracy of the decisions in intermediate phases is important for bookkeeping, for comprehensibility by human agents 47, and for analysis and improvement of the semi-automated clustered-case-management system, the primary measure of the accuracy of the case-management system is the accuracy of the ultimate resolutions of the cases. Thus, the decisions from each phase—or, equivalently, the models from each phase—are fed back (dotted arcs) to the preceding phases so that the clusters in each phase are aligned with the ultimate resolutions, effecting supervised learning at each stage from the actual ultimate human resolutions. For example, when a later-stage human agent 47 reassigns a small fraction of cases from a cluster instance 3050, this not only causes the automatic agent 52 at that stage to adjust the relevant cluster models at that stage; it also causes the automatic agents 52 at all prior stages to adjust the relevant cluster models at those stages.

Figure 4:
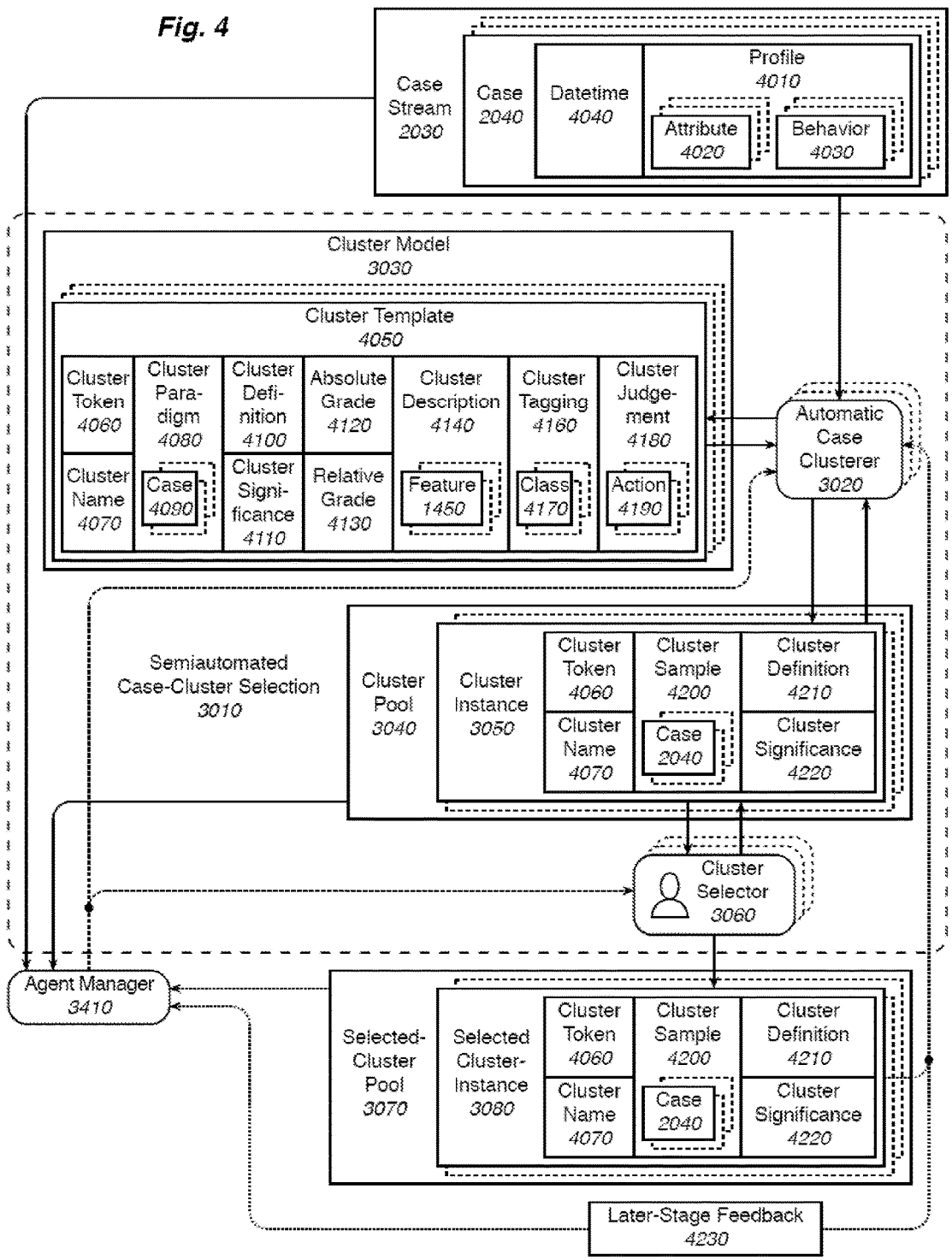
FIG. 4 is a block diagram depicting a detailed view of an example portion of a pipelined case cluster resolution system for use in connection with various embodiments.

As illustrated in information-flow diagram FIG. 4 of semi-automated case-cluster selection phase 3010, automatic case clusterers 3020 amplify case selection by grouping cases with similar attributes and behaviors into clusters 4050, so that entire groups 3050 of related cases at a time can be evaluated by cluster selectors 3060 and selected for further processing. The automatic case clusterers 3020 further speed case selection by predicting the significance 4220 of each cluster instance.

As each individual case 2040 appears in input case stream 2030, an automatic case clusterer 3020 attempts to match the case 2040 with cluster templates 4050 in case-cluster model 3030 by comparing the case to cluster paradigms 4080 and logico-mathematical cluster-template definitions 4100. If the new case matches an existing template, the paradigm and definition of the matching template and those of its neighbors in the clustering space are adaptively adjusted as necessary to accommodate the additional case, in accordance with the adaptive clustering method used. If the new case does not adequately match any preexisting template, a new template is created for the exceptional case, and is given a unique cluster token 4060; its paradigm is initialized to that case, its definition is initialized in relation to its neighbors, and the paradigms and definitions of its neighbors are adaptively adjusted to accommodate the nascent additional cluster, in accordance with the adaptive clustering method used.

Automatic case clusterers 3020 may use supervised clustering algorithms associating case attributes 4020 with case behaviors 4030, in addition to unsupervised clustering algorithms in the space of attributes and behaviors. Individual dimensions of attributes and behaviors may be compared binarily (equal versus unequal); topologically (e.g. less than, equal, or greater than); or metrically—including linearly, nonlinearly, or nonparametrically. Login IDs may for example be treated as categorical variables compared for exact match; as ordered variables compared alphanumerically or by other culture-specific sort rules; as strings in a discrete space compared by Damerau-Levenshtein or other edit distance; or as points in a real space compared by empirical mistyping probability.

As an example, in an embodiment for detecting and resolving website fraud and security issues, the types of attributes 4020 that can be analyzed include:
user attributes, such as login ID, user name, password, cookie, query-string session ID, cookie user ID, cookie session ID, authorization ID, account ID, physical address, mailing address, email address, telephone number, account type, account value, account age . . . .
user-agent attributes, such as browser or other application, plug-ins, operating system, hardware, screen size, language preferences, font preferences, MAC address . . . .
client IP-address attributes, such as IP-address class, geolocation, geoterritory, carrier, carrier type . . . .
network attributes, such as traceroute length, speed, congestion, error rate . . . .
service attributes, such as service application name, module name, version number, release date . . . .
server attributes, such as data center, IP address, port number, operating system name, version, hardware . . . .
page attributes, such as URL, name, title, type, business function, form parameters, layout, linkage, security level, access level, privilege level, size, HTTP status code . . . .
website personnel attributes, such as login ID, name, work shift, job title, privileges, physical address, mailing address, email address, telephone number . . . .
and the types of website session behaviors that can be analyzed include:
session flow
referrer flow
quickness
repetition
error rate
duration
IP-address change
user-agent change
preference change
URL manipulation
HTTP header manipulation
form manipulation
and the types of entities that can be analyzed and acted on include:
users, as identified for example by login ID, user name, cookie, MAC address, query-string session ID, cookie user ID, cookie session ID, authorization ID, account ID, account type, physical address, mailing address, email address, telephone number . . . .
user-agents, as identified by browser or other application, plug-ins, operating system, hardware, screen size, language preferences, font preferences . . . .
client IP addresses, as identified for example by IP-address class, geolocation, geoterritory, carrier, carrier type . . . .
networks, as identified by traceroute, speed, congestion, error rate . . . .
services, as identified by application name, module name, version number, release date . . . .
servers, as identified by data center, IP address, port number, operating system name, version, hardware . . . .
pages, as identified for example by URL, name, title, type, business function, form parameters, layout, linkage, security level, access level, privilege level, HTTP status code . . . .

website personnel, as identified for example by login ID, name, work shift, job title, privileges, physical address, mailing address, email address, telephone number . . . .

Cluster-template 4050 definitions may be Boolean or fuzzy; mutually exclusive or overlapping; flat, hierarchical, or heterarchical; as befits the domain, the clustering method, and the range at each stage, with roughly equivalent overall effect. Thus a fuzzy clustering method probabilistically assigning a case 2040 to plural clusters, each of which probabilistically results in a resolution, can be approximated by an overlapping clustering method definitely assigning a case to plural overlapping clusters, which can in turn be approximated by a partitioning clustering method assigning each case to exactly one cluster with potentially plural resolutions.

As each incoming case 2040 is assigned to a cluster template 4050, an automatic case clusterer 3020 looks up that cluster in cluster pool 3040, as identified by cluster token 4060. If the cluster does not already exist in the pool, a new cluster instance 3050 is created for it for possible selection by a cluster selector 3060. Either way, the new case is added to cluster sample 4200, and cluster-instance definition 4210 is adjusted accordingly. In general, the cluster sample 4200 and cluster-instance definition 4210 represent subsets of the corresponding cluster-template paradigm 4080 and cluster-template definition 4100.

To adapt to dynamic environments wherein different types of cases arise, evolve, divide, merge, and perish, case clusterers 3020 not only create new cluster templates 4050 in cluster model 3030 as new types of cases 2040 arise in input case stream 2030, and adapt existing cluster templates 4050 by adjusting cluster-template paradigms 4080 and cluster-template definitions 4100 as new cases are added to the templates and their neighbors, but also split and merge templates 4050 as cases 2040 are assigned to different clusters, and delete obsolete templates 4050 as the last old cases 2040 are removed from them.

To stabilize the cluster templates 4050 so that a given cluster will remain recognizable to cluster selectors 3060 and to agents in other stages from hour to hour, day to day, and week to week, the effective duration of cluster model 3030 is designed to be at least as long as that of cluster pool 3040, and long enough to accommodate transient clusters without displacing clusters enduring for a week or more. Each case 2040 is stamped with a datetime 4040 used to age cases. Whenever a case 2040 ages beyond a configurable modeling-frame duration, such as 3 weeks for cluster model 3030, that case 2040 is subtracted from the model 3030, and formerly neighboring cluster-template paradigms 4080 and cluster-template definitions 4100 are adjusted accordingly. Likewise, whenever a case 2040 ages beyond a configurable analysis-window duration, such as 3 days for cluster pool 3040, that case 2040 is removed from the pool 3040, and formerly neighboring cluster-instance samples 4200 and cluster-instance definitions 4210 are adjusted accordingly. In a similar fashion, whenever the cluster model 3030 or cluster pool 3040 is full, the oldest case 2040 is dropped and the relevant cluster templates 4050 and instances 3050 adjusted accordingly. When the last case 2040 is subtracted from a cluster template 4050, that template 4050 is deleted from the cluster model 3030. Likewise, when the last case 2040 is deleted from a cluster instance 3050, that instance 3050 is deleted from the cluster pool 3040.

An automatic or human cluster selector 3060 transfers significant cluster instances 3050 from cluster pool 3040 to selected-cluster pool 3070 as selected cluster-instances 3080; and may also discard insignificant cluster instances 3050 from the cluster pool 3040. In a more-sophisticated embodiment, case clusterers 3020 may continue to add new cases 2040 to a selected cluster-instance 3050 until cluster-analysis phase 3150 in order to reduce the processing latency.

Upon selecting or discarding a cluster instance 3050 from the cluster pool 3040, a cluster selector 3060 may create or edit a human-recognizable name 4070 for the cluster template, which is then stored in the cluster template 4050 in the cluster model 3030 and thenceforth applied to label any instance 3050 of that template 4050 in the cluster pool 3040.

Automatic case clusterers 3020 track the significance 4110 of each cluster template 4050, which is used to determine the frequency or prominence which with instances 3050 of the cluster are presented for selection in cluster pool 3040 to cluster selectors 3060. The significance 4110 of a cluster template 4050 depends on how often an instance 3050 of that cluster is selected, rejected, or ignored by cluster selectors 3060 and on the number of cases 2040 in each such instance 3050. In a simple embodiment, the cluster-template significance 4110 is computed as the selection frequency minus the discard frequency, divided by the view frequency during the modelling frame; and the cluster-instance significance 4220 is computed as the cluster-template significance 4110 times the logarithm of the cluster-instance case frequency:

cluster-template significance=(selection frequency−discard frequency)/view frequency cluster-instance significance=cluster-template significance×log(cluster-instance case frequency)

In situations where cluster selectors 3060 are selecting cluster-instances 3050 for different purposes, separate cluster-model significances 4110, cluster-instance significances 4220, and selected-cluster pools 3040 are maintained for each purpose.

Information-flow diagram FIG. 5 illustrates semi-automated case-cluster prioritization phase 3090, in which automatic cluster rankers 3100 multiply case prioritization by ranking whole clusters 3080 of related cases 2040 together, permitting cluster prioritizers 3140 to appraise entire groups 3130 of related cases 2040 simultaneously and prioritize them for further processing, aided by the absolute grade 4120 and relative grade 4130 automatically assigned to each cluster instance 3080 as a prediction of its priority.

Automatic cluster rankers 3100 use a supervised learning algorithm associating clusters with absolute and relative priorities based on feedback from cluster prioritizers 3140 and from later processing phases.

Absolute grade 4120 in cluster template 4050 and absolute grade 5010 in cluster instance 3130 represent configurably quantized absolute priorities (e.g. low, medium, high); while cluster-template relative grade 4130 and cluster-instance relative grade 5020 represent well-ordered sequence priorities. In one embodiment, the relative priorities are represented implicitly by position in an ordered structure such as an array, list, or queue; while the absolute priority is represented by boundaries partitioning that ordered structure.

Cluster prioritizers 3140 may explicitly reassign a cluster's absolute priority, and may alter the implicit relative sequence priority by repositioning a cluster instance 3130 within ranked-cluster list 3120 or, in some embodiments, directly in the prioritized-cluster queue 3150.

As each selected cluster instance 3080 appears in input selected-cluster pool 3070, an automatic cluster ranker 3100 tries to identify the appropriate cluster template 4050 in case-cluster model 3030 by its cluster token 4060. If a match already exists, the paradigm 4080 and definition 4100 of the matching template 4050 and its neighbors are adaptively adjusted to accommodate the additional cluster instance 3080, in accordance with the clustering algorithm used. If no match is found, a new template 4050 is created for the exceptional cluster instance 3080; its cluster token 4060, cluster name 4070, cluster paradigm 4080, and cluster definition 4100 are initialized from the corresponding fields in the cluster instance 3080; and its cluster grades 4120, 4130 are initialized according to its case frequency and to the average cluster grades 4120, 4130 of existing neighboring templates 4050 weighted by their similarity to the new cluster, for example as:

$$\text{new-cluster grade}=\log(\text{new-cluster case frequency})\times \Sigma_{\{neighboring\ cluster\}}(\text{neighboring-cluster grade}\times \text{similarity}(\text{new cluster},\text{neighboring cluster}))$$

where the cluster similarity is determined in accordance with the clustering algorithm used. In either case, the cluster ranker 3100 inserts the selected cluster as ranked cluster 3130 into ranked-cluster list 3120, setting ranked-cluster grade 5020 from the cluster-template grade 4130, and the remaining fields from the input selected cluster 3080.

In one embodiment, the absolute priority 10010 in cluster-template grade 5040 is maintained as a decaying average of absolute priorities assigned to instances 3130 of that template 4050 by cluster prioritizers 3140, and quantized in ranked-cluster grade 5020 upon insertion into ranked-cluster list 3120. In a simpler embodiment, it is maintained as the most-recent absolute priority assigned by a cluster prioritizer 3140 to an instance 3130 of that cluster.

As depicted in information-flow diagram FIG. 6, in semi-automated case-cluster investigation phase 3170, automatic cluster analyzers 3180 amplify case analysis by analyzing entire clusters 3160 of similar cases 2040, so that whole groups 3210 of related cases 2040 at a time can be analyzed by cluster investigators 3220 for further processing, based on descriptive sets 6070 of features 6080 automatically extracted for each cluster instance 3080.

A cluster investigator 3220 may eject cases 2040 from an analyzed cluster instance 3210, in which case ranked-cluster definition 4210 and cluster sample 4200 is adjusted accordingly. In a single-purpose system, if the ejected cases 2040 are still within the modeling time window, then they are returned to the front of case stream 2030, and removed from the corresponding cluster model 3030, as identified by cluster token 4060, with accordant adjustments to the cluster paradigm 4080 and cluster definition 4100 of the model 3030; and likewise for the caches of other preceding phases. In this way, expert feedback is used to refine the cluster models 3030 themselves. A cluster analyst may also split a cluster instance 3050 into separate clusters or merge separate cluster instances 3050 into a single cluster instance 3050, with, in a single-purpose system, concomitant changes to the corresponding cluster models 3030. In embodiments using hierarchical clusters, a cluster analyst may also perform standard hierarchy editing operations, such as moving clusters within and between levels.

FIG. 7 is an information-flow diagram of semi-automated case-cluster classification phase 3250, containing automatic cluster systematizers 3260 that boost case classification by automatically systematizing whole clusters 3240 of associated cases 2040, enabling cluster classifiers 3300 to examine entire clusters 3240 simultaneously and prepare them for further processing, on the basis of sets 7070 of classes 7080 assigned automatically to each cluster instance 3240.

Cluster systematizers 3260 use a supervised learning algorithm associating clusters 3240 with classes 7080 based on feedback from human cluster classifiers 3300. A cluster classifier 3260 classifies a presented systematized cluster 3240 tagged with classes 7080 within a cluster class 7070. The types of classifications include, within the field of fraud & security:

session hijacking
scraping
password guessing
money laundering
denial of service
infiltration
exfiltration
SQL injection Information-flow diagram FIG. 8 depicts semi-automated case-cluster resolution phase 3330, wherein the resolution of cases 2040 is amplified by automatic cluster judges 3340 that automatically judge related cases 2040 a whole cluster 3320 at a time in order that cluster resolvers 3380 can resolve entire clusters 3400 of cases 2040 at once, based on automatically assembled menus 8070 of recommended remedial actions 8080 for each cluster instance 3370. The types of remedial actions include, within the field of fraud & security:

blocking clients
delaying clients
diverting clients to harmless webpages
deceiving clients with misinformation
warning victims through independent channels
warning victims with personally obvious details
reversing account transactions
blocking account transactions
monitoring suspicious accounts
closing accounts
disabling pages
redirecting pages
referring the case for further analysis
referring the case to outside authorities
disciplining personnel Thus, techniques to automatically cluster related cases 2040 into clusters 3050 that may be resolved all together have been presented. This result may be achieved by automatically clustering related cases 204 into clusters 3050 according to their expected intermediate and ultimate resolutions and then feeding the clusters 3050 into a semi-automated pipelined case cluster resolution system 50 (including cluster selector 3060 as well as stages 3090, 3170, 3250, and 3330) in order to resolve entire clusters 3400 of cases 2040 at once. Thus, entire groups of cases 2040 can be dealt with together rather than individually, and much of the case processing may be done automatically by computer to increase speed and accuracy.

While various embodiments of the present disclosure have been particularly shown and described, it will be understood by those skilled in the art that various changes in form and details may be made therein without departing from the spirit and scope of the present disclosure as defined by the appended claims.

For example, it should be understood that although various embodiments have been described as being methods, software embodying these methods is also included. Thus, one embodiment includes a tangible computer-readable medium (such as, for example, a hard disk, a floppy disk, an optical disk, computer memory, flash memory, etc.) programmed with instructions, which, when performed by a computer or a set of computers, cause one or more of the methods described in various embodiments to be performed. Another embodiment includes a computer that is programmed to perform one or more of the methods described in various embodiments.

Finally, it should be understood that all embodiments that have been described may be combined in all possible combinations with each other, except to the extent that such combinations have been explicitly excluded.

Finally, even if a technique, method, apparatus, or other concept is specifically labeled as "conventional," Applicant makes no admission that such technique, method, apparatus, or other concept is actually prior art under 35 U.S.C. § 102 or 35 U.S.C. § 103, such determination being a legal determination that depends upon many factors, not all of which are known to Applicant at this time.

What is claimed is:

1. A method, performed by a computing device, of efficiently resolving network irregularity cases within a system, the method comprising:
receiving a set of event descriptions regarding network traffic events that occurred within the system and properties of the system, receiving the set of event descriptions including sniffing network packets;
automatically generating a set of web sessions within the system by finding patterns within the sniffed network packets of the set of event descriptions and properties within the system;
running an automated clustering agent to automatically create a plurality of clusters of related web sessions based on similarities between the related web sessions, each cluster including a plurality of web sessions, wherein:
running the automated clustering agent to automatically create the plurality of clusters of related web sessions includes matching web sessions of the set of web sessions to particular cluster templates of a cluster model, thereby generating a plurality of cluster instances, each cluster instance including a plurality of related web sessions that satisfy a set of rules within a respective cluster template; and
the automated clustering agent is configured to create respective cluster templates based on respective similarities between respective related web sessions of the set of web sessions, each created cluster template being assigned a respective set of rules that define the respective related web sessions for that created cluster template; and
processing a set of the clusters of web sessions through a pipelined web session cluster resolution scheme, the pipelined web session cluster resolution scheme involving a plurality of computerized agents operating in a defined order, the pipelined web session cluster resolution scheme resulting in a resolution of each web session of a cluster of the plurality of clusters of related web sessions, each web session having a same resolution as each other web session in its respective cluster, wherein processing the set of the clusters of web sessions through the pipelined web session cluster resolution scheme includes having a cluster selector agent:
modify the plurality of related web sessions within a particular cluster instance; and
select particular cluster instances for further processing;

wherein:
the automated clustering agent is further configured to apply supervised learning techniques to selectively modify the respective set of rules for cluster templates based on:
whether the cluster selector agent has modified the plurality of related web sessions within a cluster instance of a respective cluster template; and
whether the cluster selector agent has selected a particular cluster instance of a respective cluster template;
processing the set of the clusters of web sessions through the pipelined web session cluster resolution scheme further includes:
having a computerized cluster ranking agent rank the selected particular cluster instances based on grade information stored within respective cluster templates to generate a ranked cluster list;
having a computerized cluster systematizer agent determine diagnoses of each cluster instance within the ranked cluster list based on a set of class templates of the cluster model, wherein determining the diagnosis of a particular cluster instance of the ranked cluster list includes determining that the diagnosis is a particular type of cyberattack; and
having a computerized cluster judge agent determine a set of remedial actions for each cluster instance within the ranked cluster list based on the determined diagnoses for that respective cluster instance and on a set of action templates of the cluster model, wherein determining the set of remedial actions for the particular cluster instance includes determining that the set of remedial actions includes blocking access to a network resource; and
the method further comprises, for each cluster instance, applying the set of remedial actions to all web sessions within that cluster instance, wherein applying the set of remedial actions for the particular cluster instance includes blocking access to a network resource for each web session within the particular cluster instance.

2. The method of claim 1 wherein automatically generating the set of web sessions by finding patterns is performed using unsupervised machine learning based on statistical techniques.

3. The method of claim 1 wherein automatically generating the set of web sessions by finding patterns is performed using supervised machine learning based on statistical techniques.

4. The method of claim 1 wherein:
the cluster selector agent is initially a person; and
upon a confidence threshold for the cluster model being exceeded, utilizing an automated cluster selector agent in lieu of the initial person.

5. The method of claim 1 wherein processing the set of the clusters of web sessions through the pipelined web session cluster resolution scheme further includes:
having a computerized cluster analyzer agent determine features of each cluster instance within the ranked cluster list based on a set of feature templates of the cluster model;
having a cluster investigator agent extract an essential subset of the features of cluster instances within the ranked cluster list;
having the cluster investigator agent selectively remove cluster instances from the ranked cluster list which do not have any features within their respective essential subsets; and automatically modifying the cluster model based on the selectively removed cluster instances.

6. The method of claim 1 wherein:
determining that the diagnosis is a particular type of cyberattack includes determining that the diagnosis is a Trojan Horse software infection; and
determining that the set of remedial actions includes blocking access to the network resource includes quarantining a file infected by the Trojan Horse software infection.

7. The method of claim 1 wherein determining that the diagnosis is a particular type of cyberattack includes determining that the diagnosis is session hijacking.

8. The method of claim 1 wherein determining that the diagnosis is a particular type of cyberattack includes determining that the diagnosis is scraping.

9. The method of claim 1 wherein determining that the diagnosis is a particular type of cyberattack includes determining that the diagnosis is infiltration.

10. The method of claim 1 wherein determining that the diagnosis is a particular type of cyberattack includes determining that the diagnosis is exfiltration.

11. The method of claim 1 wherein determining that the diagnosis is a particular type of cyberattack includes determining that the diagnosis is database code injection.

12. The method of claim 1 wherein determining that the set of remedial actions includes blocking access to the network resource includes closing an account.

13. The method of claim 1 wherein determining that the set of remedial actions includes blocking access to the network resource includes disabling a web page.

14. The method of claim 1 wherein determining that the set of remedial actions includes blocking access to the network resource includes blocking an account transaction.

15. A computer program product comprising a non-transitory computer-readable medium storing a set of instructions, which, when executed by a computing device, causes the computing device to efficiently resolve network irregularity cases within a system by:
receiving a set of event descriptions regarding network traffic events that occurred within the system, receiving the set of event descriptions including sniffing network packets;
automatically generating a set of web sessions within the system by finding patterns within the sniffed network packets of the set of event descriptions and properties within the system;
running an automated clustering agent to automatically create a plurality of clusters of related web sessions based on similarities between the related web sessions, each cluster including a plurality of web sessions, wherein:
running the automated clustering agent to automatically create the plurality of clusters of related web sessions includes matching web sessions of the set of web sessions to particular cluster templates of a cluster model, thereby generating a plurality of cluster instances, each cluster instance including a plurality of related web sessions that satisfy a set of rules within a respective cluster template; and
the automated clustering agent is configured to create respective cluster templates based on respective similarities between respective related web sessions of the set of web sessions, each created cluster template being assigned a respective set of rules that define the respective related web sessions for that created cluster template; and processing a set of the clusters of web sessions through a pipelined web session cluster resolution scheme, the pipelined web session cluster resolution scheme involving a plurality of computerized agents operating in a defined order, the pipelined web session cluster resolution scheme resulting in a resolution of each web session of a cluster of the plurality of clusters of related web sessions, each web session having a same resolution as each other web session in its respective cluster, wherein processing the set of the clusters of web sessions through the pipelined web session cluster resolution scheme includes having a cluster selector agent:
modify the plurality of related web sessions within a particular cluster instance; and
select particular cluster instances for further processing;
wherein:
the automated clustering agent is further configured to apply supervised learning techniques to selectively modify the respective set of rules for cluster templates based on:
whether the cluster selector agent has modified the plurality of related web sessions within a cluster instance of a respective cluster template; and
whether the cluster selector agent has selected a particular cluster instance of a respective cluster template;
processing the set of the clusters of web sessions through the pipelined web session cluster resolution scheme further includes:
having a computerized cluster ranking agent rank the selected particular cluster instances based on grade information stored within respective cluster templates to generate a ranked cluster list;
having a computerized cluster systematizer agent determine diagnoses of each cluster instance within the ranked cluster list based on a set of class templates of the cluster model, wherein determining the diagnosis of a particular cluster instance of the ranked cluster list includes determining that the diagnosis is a particular type of cyberattack; and
having a computerized cluster judge agent determine a set of remedial actions for each cluster instance within the ranked cluster list based on the determined diagnoses for that respective cluster instance and on a set of action templates of the cluster model, wherein determining the set of remedial actions for the particular cluster instance includes determining that the set of remedial actions includes blocking access to a network resource; and
the set of instructions, when executed by the computing device, further cause the computing device to efficiently resolve web sessions within the system by, for each cluster instance, applying the set of remedial actions to all web sessions within that cluster instance, wherein applying the set of remedial actions for the particular cluster instance includes blocking access to a network resource for each web session within the particular cluster instance.

16. An apparatus comprising:
memory; and
processing coupled to the memory, configured to efficiently resolve network irregularity cases within a system by:

receiving a set of event descriptions regarding network traffic events that occurred within the system, receiving the set of event descriptions including sniffing network packets;

automatically generating a set of web sessions within the system by finding patterns within the sniffed network packets of the set of event descriptions and properties within the system;

running an automated clustering agent to automatically create a plurality of clusters of related web sessions based on similarities between the related web sessions, each cluster including a plurality of web sessions, wherein:

running the automated clustering agent to automatically create the plurality of clusters of related web sessions includes matching web sessions of the set of web sessions to particular cluster templates of a cluster model, thereby generating a plurality of cluster instances, each cluster instance including a plurality of related web sessions that satisfy a set of rules within a respective cluster template; and the automated clustering agent is configured to create respective cluster templates based on respective similarities between respective related web sessions of the set of web sessions, each created cluster template being assigned a respective set of rules that define the respective related web sessions for that created cluster template; and processing a set of the clusters of web sessions through a pipelined web session cluster resolution scheme, the pipelined web session cluster resolution scheme involving a plurality of computerized agents operating in a defined order, the pipelined web session cluster resolution scheme resulting in a resolution of each web session of a cluster of the plurality of clusters of related web sessions, each web session having a same resolution as each other web session in its respective cluster, wherein processing the set of the clusters of web sessions through the pipelined web session cluster resolution scheme includes having a cluster selector agent:

modify the plurality of related web sessions within a particular cluster instance; and select particular cluster instances for further processing;

wherein:

the automated clustering agent is further configured to apply supervised learning techniques to selectively modify the respective set of rules for cluster templates based on:

whether the cluster selector agent has modified the plurality of related web sessions within a cluster instance of a respective cluster template; and whether the cluster selector agent has selected a particular cluster instance of a respective cluster template;

processing the set of the clusters of web sessions through the pipelined web session cluster resolution scheme further includes:

having a computerized cluster ranking agent rank the selected particular cluster instances based on grade information stored within respective cluster templates to generate a ranked cluster list;

having a computerized cluster systematizer agent determine diagnoses of each cluster instance within the ranked cluster list based on a set of class templates of the cluster model, wherein determining the diagnosis of a particular cluster instance of the ranked cluster list includes determining that the diagnosis is a particular type of cyberattack; and having a computerized cluster judge agent determine a set of remedial actions for each cluster instance within the ranked cluster list based on the determined diagnoses for that respective cluster instance and on a set of action templates of the cluster model, wherein determining the set of remedial actions for the particular cluster instance includes determining that the set of remedial actions includes blocking access to a network resource; and the set of instructions, when executed by the computing device, further cause the computing device to efficiently resolve web sessions within the system by, for each cluster instance, applying the set of remedial actions to all web sessions within that cluster instance, wherein applying the set of remedial actions for the particular cluster instance includes blocking access to a network resource for each web session within the particular cluster instance.

* * * * *